United States Patent [19]

Okawa

[11] Patent Number: 5,741,483
[45] Date of Patent: Apr. 21, 1998

[54] INDUSTRIAL PRESERVATIVE ANTIFUNGAL COMPOSITION AND UNDERWATER ANTIFOULING COMPOSITION

[75] Inventor: Shozo Okawa, Ibaraki, Japan

[73] Assignee: Rohm and Haas Company, Philadelphia, Pa.

[21] Appl. No.: 642,064

[22] Filed: May 3, 1996

[30] Foreign Application Priority Data

May 10, 1995 [JP] Japan .................................. 7-111689

[51] Int. Cl.$^6$ .................... A01N 43/80; A01N 43/30; A61K 31/74
[52] U.S. Cl. .................. 424/78.09; 514/372; 514/464; 514/722; 523/122
[58] Field of Search ..................... 514/372, 464, 514/722; 424/78.09; 523/122

[56] References Cited

U.S. PATENT DOCUMENTS

| | | | |
|---|---|---|---|
| 2,508,916 | 5/1950 | Harris et al. | 514/722 |
| 2,550,737 | 2/1951 | Wachs | 167/24 |
| 3,338,783 | 8/1967 | Popsak | 514/464 |
| 3,761,488 | 9/1973 | Lewis et al. | 260/302 |
| 5,464,850 | 11/1995 | Voo et al. | 514/372 |
| 5,466,382 | 11/1995 | Downey et al. | 514/372 |
| 5,468,759 | 11/1995 | Hsu | 514/722 |

FOREIGN PATENT DOCUMENTS

| | | | |
|---|---|---|---|
| 1185897 | 4/1985 | Canada | 514/464 |
| 375367 A | 6/1990 | European Pat. Off. | |
| 2816474 | 10/1979 | Germany | 514/464 |
| 79062316 | 5/1979 | Japan . | |
| 62156173 | 12/1985 | Japan . | |
| 63044504 | 8/1986 | Japan . | |
| 4230303 | 8/1992 | Japan . | |
| 4011878 | 2/1994 | Japan . | |

OTHER PUBLICATIONS

C. Tomlin, "The Pesticide manual–Tenth Edition", 1994, British Crop Protection Council, pp. 817–818 and 908–909.
Handbook of Agricultural Chemicals (Written In Japanese), 1994 Edition, pp. 475–476, p. 644, Published By Japanese Association of Prevention of Plant Diseases; Science vol. 105, p. 530 (2947).

*Primary Examiner*—Peter F. Kulkosky
*Attorney, Agent, or Firm*—Julie J.L. Cheng

[57] ABSTRACT

An industrial preservative antifungal composition containing and underwater antifouling composition comprising 4,5-dichloro-2-n-octyl-4-isothiazoline-3-one and/or 2-n-octyl-4-isothiazoline-3-one or salts thereof and 5-[2-(2-butoxyethoxy)ethoxymethyl]-6-propyl-1,3-benzodioxole and/or octachlorodipropyl ether as supplementary agent(s).

7 Claims, No Drawings

INDUSTRIAL PRESERVATIVE ANTIFUNGAL COMPOSITION AND UNDERWATER ANTIFOULING COMPOSITION

This invention relates to a nobel industrial preservative antifungal composition which is added or coated on industrial resource materials to prevent breakdown of the industrial raw materials and products such as emulsion paint, oil-based paint, electrodeposition paint, organic adhesives, pastes, clay, ink, cutting oil, grinding oil, wood materials, leather, various fibers, and white water from production of paper, etc. caused by bacteria, yeasts, filamentous fungi, algae, etc. And, this invention relates also to a low-toxicity underwater antifouling composition which can be added in the paints which are used to coat the submerged marine structure such as ships, culturing nets, fixt net, oil well drill in the ocean, submerged marine base, buoy, water conduit of power generating stations, and bridges, etc. to prevent attachment and growth of aquatic organisms that grow by attaching on the surface of the submerged structure, to show the antifouling effect for a long period of time.

4,5-Dichloro-2-n-octyl-4-isothiazoline-3-one ("Compound A", hereinafter) and 2-n-octyl-4-isothiazoline-3-one ("Compound A'", hereinafter) or the salts of these strong acids are known as the agents that can exterminate microorganisms such as bacteria (Specification, U.S. Pat. No. 3,761,488).

5-[2-(2-Butoxyethoxy) ethoxymethyl]-6-propyl-1,3-benzodioxole ("Compound B hereinafter) is known for the effect of preventing ozone effect in the growing tobacco plant or as a supplementary agent for the insecticide pyrethrin [Handbook of Agricultural Chemicals (written in Japanese), 1994 Edition, pages 475–476, page 644, published by Japanese Association of Prevention of Plant Diseases; Science, Volume 105, page 530 (2947); and U.S. Pat. No. 2,550,737].

And, octachlorodipropyl ether ("Compound C", hereinafter) is known as the tick killer to be used together with pyrethroid insecticides [Japanese Kokai Patent, HEI 4-230303(1992)], and also as an antifouling agent [Japanese Kokai Patent, SHO 62-156173(1987)].

To protect industrial resource materials such as industrial raw materials or products from breakdown caused by contamination of bacteria, yeasts, and fungus, presence or growth of various microorganisms on the surface or interior of these materials must be prevented non-selectively and completely. However, the industrial preservative antifungal agents currently available for such purpose are governed by a strict regulation because of its strong skin irritating property, or if the amount being used is reduced, it tends to show a lower preservative antifungal effect, or often the effect does not remain for a long period of time.

Although the Compound A and Compound A' to be used in this invention can show biocidal activity against microorganisms such as bacteria, but they showed the above-described flaws when used as industrial preservative antifungal agent, and they do not have a satisfactory effect when used alone.

Therefore, a new industrial preservative antifungal agent having excellent preservative antifungal effect in preventing survival and growth of various industrially harmful microorganisms for a long period of time and can sustain the effect for a long period of time, even used in a small quantity, is in demand, to replace the conventional industrial anti-preservative antifungal agent.

On the other hand, marine animals such as Balnus, Ascidia, Serpula, Mytilus, Spirorbis, Bugula, Hydrazoa, etc, and algae such as Entermorpha and Ulva, etc. can attach and grow on the surface of the submerged marine structures to cause various damage. For example, if marine organisms attach and grow on ship's hull, it lowers the speed of the ship and increases the fuel cost. And, if marine organisms attach and grow on the surface of a submerged harbor facilities, immobilized in water or on the surface water, the equipment may not function well. If the organisms attach and grow on the culturing nets used in ocean farms or fixed net, they may clog up the net to kill the fishes or cause a damage to the net.

Organotin compounds have been used often to prevent the damages to the underwater marine structure caused by such marine organisms. However, use of organotin compounds has been strictly regulated because they have high toxicity and therefore are not desirable due to safety and environment reasons.

Due to this situation, it is desirable to develop an underwater antifouling agent that has a low toxicity to mammals, can be used safely, and has a long persisting antifouling effect.

In order to develop a new industrial preservative antifungal agent and underwater antifouling agent that can meet the above-said requirements, the present inventors have tested a wide variety of compounds to study its physiological activity. As a result, it was discovered that Compound A and Compound A', when combined with Compound B or Compound C and used on various microorganisms, can drastically increase the biocidal effect.

Furthermore, it was discovered that the composition containing the Compound A or Compound A' and Compound B or Compound C, in small quantity, was useful as an industrial preservative angifungal agent that can prevent growth of various microorganisms for a long period of time, and the paint containing such composition can serve as a long-lasting underwater antifouling agent which is safe and has excellent antifouling activity.

Thus, the first invention is an industrial preservative antifungal composition containing 4,5-dichloro-2-n-octyl-4-isothiazoline-3-one or 2-n-octyl-4-isothiazoline-3-one or its salts as the effective biocidal component, and containing also 5-[2-(2-butoxyethoxy) ethoxymethyl]-6-propyl-1,3-benzodioxole or octachlorodipropyl ether as its supplementary agent.

And, the second invention is an underwater antifouling composition, containing 4,5-dichloro-2-n-octyl-4-isothiazoline-3-one or 2-n-octyl-4-isothiazoline-3-one or its salts as the effective antifouling components, and also containing 5-[-2-(2-butoxyethoxy) ethoxymethyl]-6-propyl-1, 3-benzodioxole as the supplementary agent, and containing octachlorodipropyl ether as the effective second antifouling component.

Chemical names and chemical structures of the above-said components which are used in the compositions of the first and second inventions are shown below.

Compound A: 4,5-dichloro-2-n-octyl-4-isothiazoline-3-one

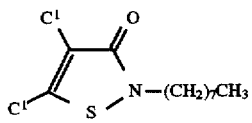

Compound A': 2-n-Octyl-4-isothiazoline-3-one

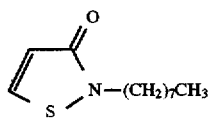

Incidentally, Compound A and Compound A' may be used in an acid-added salt form in conjunction with sulfuric acid, hydrochloric acid, hydrobromic acid, nitric acid, or phosphoric acid.

Compound B: 5-[2-(2-Butoxyethoxy)ethoxymethyl]-B-propyl-1,3-benzodioxole

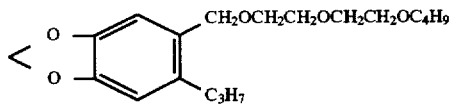

Compound C: Octachlorodipropyl ether

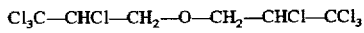

And, in the compositions of the first and second inventions, benzothiazole biocide such as 1,2-benzoisothiazoline-3-one (Compound A", hereinafter) may be used additionally to replace the above-said Compound A or Compound A'.

It was discovered that, with the industrial preservative antifungal composition and marine antifouling composition of this invention, addition of Compound B or Compound C to the Compound A or Compound A' had significantly and synergistically increased the preservative antifungal activity and underwater antifouling activity of the Compound A or Compound A'.

The industrial preservative antifungal composition of the first of this invention is explained comprehensively in the following. Method of preparation and method of use of the industrial preservative antifungal composition of the first invention are as follows.

The industrial preservative antifungal composition of the first invention can be prepared by the following method. Thus, the preservative angifungal composition of the first invention is prepared by mixing Compound A (or Compound A') with Compound B (or Compound C) at a proper weight ratio, and, if necessary or if so desired, a proper carrier is blended, or suitable supplementary agent(s), such as surface activating agent, binder, stabilizer, etc. are added supplementarily to prepare a homogeneous mixture, and this mixture is prepared as hydrated agent, emulsion, liquid, or flowable agent (sol agent), and so on.

Total content of Compound A (or A') and Compound B (or C) in the thus-prepared preservative antifungal composition of the first invention, if it is a hydrated agent, emulsion, liquid, or flowable agent, can be set in 0.1–90% to (weight %, same hereinafter) range, based on the weight of the total preparation. In this case, the ratio of Compound B or Compound C and the Compound A or Compound A' is, for example, 0.1–5 parts, preferably 0.3–3 parts, of Compound B or Compound C to 1 part of Compound A or Compound A'.

Any carriers that are used commonly in known industrial preservative antifungal agents can be used as the carrier to be added in this composition, and any of the solid or liquid can be used, without any particular restriction.

Examples of the solid carriers that can be added are mineral powder (kaolin, bentonite, clay, montmorillonite, talc, diatomaceous earth, mica, vermiculite, gypsum, calcium carbonate, apatite, white carbon, calcium oxide, silicate sand, ammonium sulfate, urea, and 80 on), plant powder (soybean powder, flour, wood powder, tobacco powder, starch, crystalline cellulose, and so on), alumina, silicate salts, sugar polymers, highly dispersed silicic acid, waxes, semi-solid oils and so on.

Examples of the liquid carriers that can be added are water, alcohols (methyl alcohol, ethyl alcohol, n-propyl alcohol, isopropyl alcohol, n-butyl alcohol, ethyleneglycol, benzyl alcohol, and so on), aromatic hydrocarbons (benzene, toluene, xylene, ethylbenzene, chlorobenzene, cumene, methyl naphthalene, and so on), halogenated hydrocarbons (chloroform, carbon tetrachloride, dichloromethane, chloroethylene, trichlorofluoromethane, dichlorodifluoromethane, and so on), ethers (ethyl ether, ethylenoxide, dioxane, tetrahydrofuran, and so on), ketones (acetone, methylethyl ketone, cyclohexanone, methylisobutyl ketone, and so on), esters (ethyl acetate, butyl acetate, ethyleneglycol acetate, amyl acetate, and so on), nitriles (acetonitrile, propionitrile, acrylonitrile, and so on), sulfoxides (dimethylsulfoxide and so on), glycol ethers (ethyleneglycol monomethyl ether, ethyleneglycol monoethyl ether, 1-methoxy-2-propanol, and so on), amines (ethylamine, dimethylamine, triethylamine, isobutylamine, and so on), aliphatic or alicyclic hydrocarbons (n-hexane, cyclohexane, and so on), industrial gasoline (petroleum ether, solvent naphtha, and so on), and petroleum fraction (paraffines, kerosene, light oil, and so on).

In case of preparing the preservative antifungal composition of the first invention as an emulsion, hydrated agent or sol (flowable agent), surface activating agent may be added for a purpose of emulsification, dispersion, dissolution, wetting, foaming and diffusion. Following compounds can be mentioned as the sample of such surface activating agent, but it is not limited only to these examples.

(a) Nonionic surface activating agents, such as polyoxyethylenealkyl ether, polyoxyethylenealkyl ester, polyoxyethylene sorbitan alkyl ester, sorbitan alkyl ester and so on.

(b) Anionic surface activating agents, such as alkylbenzene sulfonate, alkyl sulfosuccinate, alkyl sulfate, polyoxyethylenealkyl sulfate, aryl sulfonate and so on.

(c) Cationic surface activating agents, like alkylamines, such as laurylamine, stearyltrimethylammonium chloride, alkyldimethylbenzylammonium chloride, and so on.

(d) Amphoteric surface activating agents, such as sulfate esters of carboxylic acid (betain type), and so on.

Beside the components described above, various supplementary agents such as polyvinyl alcohol (PVA), carboxycellulose (CMC), gum Arabic, xanthnn gum, hydroxypropylcellulose, polyvinyl acetate, gelatin, casein, sodium alginate may be added to the preservative antifungal comoposition of the first invention. And, if necessary, a proper amount of stabilizer such as antioxidant and UV absorber may be added also.

If so desired, insecticides or various preservative antifungal compounds, such as 2-(4-thiazolyl)benzimidazole (TBZ), benzyl bromoacetate, pentachlorophenol or its salts, 2,4,5,6-tetrachloro-4-methylsulfonyl pyridine, n-butyl p-benzoate, 1,2-dibromo-2,4-dicyano-butane, N-dichlorofluoromethyl-N,N'-dimethyl-N-phenyl sulfamide (PREVENTOL A4),2,4,5,6-tetrachloroisophthalonitrile, p-chloro-methaxylenol, 3-iodo-2-prooalgylbutyl carbamate (IPBC), methyl-2-benzimidazole carbamate (MBC), 5-chloro-2-methyl-4-isothiazoline-3-one, and 2-methyl-4-isothiazoline-3-one, and so on maybe added additionally to the industrial preservative antifungal composition of the first invention.

Examples of the preservative antifungal composition of the first invention is illustrated embodically, in the following Examples 1–4. However, ratio of effective components, amount of supplementary components and others are not limited by the following examples. Incidentally, "parts" shown in Examples 1–4 represent "parts, by weight".

Example 1 (Emulsion)

Compound A or Compound A' 10 parts, Compound B or Compound C 10 parts, 1-methoxy-2-propanol 65 parts, xylene 10 parts, SOLPOL 900A (name of the emulsifier, by Toho Kagaku Kogyo K.K.) 5 parts were mixed and dissolved, to obtain an emulsion.

Example 2 (Emulsion)

Compound A or Compound A' 20 parts, Compound B or Compound C 10 parts, 1-methoxy-2-propanol 55 parts, xylene 10 parts, SOLPOL 800A (name of the emulsifier, by Toho Kagaku Kogyo K.K.) 5 parts were mixed and dissolved, to obtain an emulsion.

Example 3 (Hydrated agent)

Compound A or Compound A' 2 parts, Compound B or Compound C 10 parts, lauryl sulfate 8 parts, and clay 80 parts were mixed uniformly, and pulverized, to obtain a hydrated agent.

Example 4 (Flowable agent)

Compound A or Compound A' 10 parts, Compound B or Compound C 20 parts, lauryl sulfate 2 parts, xanthan gum 2 parts, hydroxypropylcellulose 1 part, and distilled water 65 parts were mixed in a Homomixer, to obtain a flowable agent.

The industrial preservative antifungal composition of the first invention is used in the following manner. Thus, each type of formula prepared by the procedure of Example 1–4 was used directly, or diluted or dispersed in water or an appropriate organic solvent to prepare a solution or dispersion. The powder, solution or dispersion is (1) added in the various industrial raw materials or in the products during its production process, (2) coated or sprayed on the surface of various industrial raw materials or its products, or (3) the industrial raw material or its product is dipped in a diluted solution or dispersion of the industrial antifungal composition of the first invention to coat the surface or impregnate the material. Thus, various methods can be used by following the procedure which is commonly used for application of industrial preservative antifungal agent. Therefore, there is no particular restriction about the method of using the industrial preservative antifungal composition of this invention.

The underwater antifouling composition of the second invention is explained comprehensively in the following.

Although there is no particular restriction about the ratio of the Compound A (or A') and Compound B (or C) in the underwater antifouling composition of the second invention, the range of content of the compound B (or C) is 0.1–10 parts (by weight), preferably 1–3 parts, per 1 part of the Compound A (or A').

The underwater antifouling composition of the second invention may be a simple mixture of the Compound A (or Compound A') or its salt and the Compound B (or Compound C). However, this underwater antifouling composition may contain an inactive solid or liquid carrier that can carry the Compound A (or Compound A') or its salt and the Compound B (or Compound C) or its salt as the effective components. Examples of the solid carriers that can be added are one of the suitable mineral powders described above, such as alumina and silicate salt, and examples of the liquid carrier are water or various organic solvents, such as 1-methoxy-2-propanol, xylene and their mixture, that can dissolve or disperse the compounds of the effective components.

To prepare the underwater antifouling paint by adding the underwater antifouling composition of the second invention, it is proper to add the underwater antifouling composition of the second invention into a paint composition by ordinary techniques. As the means to add the underwater antifouling composition of the second invention to the paint, a mixture containing the Compound A (or A') or its salt and the Compound B (or C) in a proper mixing ratio to serve as the effective components is dissolved in an organic solvent. Or, if there is no suitable organic solvent, the mixture of the powders of effective components is pulverized and mixed mechanically and uniformly by means of a mixer such as an atomizer, etc. The underwater antifouling paint can be prepared by adding an organic solvent, surface activating agent, resin for paints, plasticizer, pigments and other supplemental components required for the paint, to the solution of the mixture of effective components or powder of the mixture of effective components thus obtained.

The resin for the paint, that can be used in the paint to which the underwater antifouling composition of the second invention is added is a film-forming resin to form a coated film on the surface of the substrate, and any resins which are commonly used for the conventional underwater antifouling paint can be used.

Examples of the resin are vinylchloride/vinyl acetate copolymers, vinyl chloride/vinlyisobutyl ether copolymers, styrene/butadiene copolymers, chlorineted rubber resins, chlorineted polypropylene resins, petroleum resins, alkyd resins, acrylic resins, phenolic resins, synthetic rubber, epoxy resins, silicone rubber, silicone resins, Teflon resins, and rosin resins, and so on.

In the underwater antifouling paint containing the underwater antifouling composition of the second invention, total content of the Compound A or Compound A' and Compound B or Compound C is 0.1–350 weight parts, preferably about 1–150 weight parts, per 100 weight parts of the resins used in the paint.

Furthermore, it is desirable to add no more than 20 weight parts, per 100 weight parts of resin, of plasticizer in the thus-prepared underwater antifouling paint.

If necessary, color pigment or dye, such as titan white, rouge, carbon, cyanin blue, cyanin green, or body pigment such as talc, baryta, zinc white, and so on may be added to the underwater antifouling paint prepared by adding the underwater antifouling composition of the second invention. Furthermore, water or organic solvent may be added to regulate the viscosity of the paint. The organic solvent to be used is the type that can dissolve or disperse the resin and other components, and there is no particular restriction.

Examples of the organic solvent that can be added in such underwater antifouling paint are alcohols (methyl alcohol, ethyl alcohol, n-propyl alcohol, isopropyl alcohol, ethyleneglycol, benzyl alcohol, and so on), aromatic hydrocarbons (benzene, toluene, xylene, ethylbenzene, chlorobenzene, cument, methyl naphthalene, and so on), halogentated hydrocarbons (chloroform, carbon tetrachloride, dichloromethane, chloroethylene, trichlorofluoromethane, dichlorodifluoromethane, and so on), ethers (ethyl ether, ethylenoxide, dioxane, tetrahydrofuran, and so on), ketones (acetone, methylethyl ketone, cyclohexanone, methylisobutyl ketone, and so on), esters (ethyl acetate, butyl acetate, ethyleneglycol acetate, amyl acetate, and so on) nitriles (acetonitrile, propionitrile, acrylonitrile, and so on), sulfoxides (dimethylsulfoxide, and so on), alcohol ethers (ethyleneglycol monomethyl ether, ethyleneglycol monoethyl ether, and so on), amines (ethylamine, dimethylamine, triethylamine, isobutylamine, and so on), aliphatic or alicyclic hydrocarbons (n-hexane, cyclohexane, and so on), industrial gasoline (petroleum ether, solvent naphtha, and so on), and petroleum fractions (paraffins, kerosene, light oil, and so on).

And, surface activating agent can be added for preparation of the antifouling paint that contains the underwater antifouling composition of the second invention, for a purpose of emulsification, dispersion, dissolution, wetting, foaming, and diffusion. Surface activating agents, identical to those added in the preservative antifungal composition of the first invention can be mentioned as the examples of such surface activating agent.

Beside these, various supplementary agents such as polyvinyl alcohol (PVA), carboxymethylcellulose (CMC), gum Arabic, polyvinyl acetate, gelatin, casein, sodium alginate and so on may be added.

Even though inclusion of only the Compound A or Compound A' and Compound B or Compound C in the underwater antifouling paint that contains the underwater antifouling composition of the second invention can show enough antifouling effect, additional ordinary antifouling/antifungal/antialgal agent may be added if necessary. Examples of such ordinary antifouling/antifungal/antialgal agent are 1-(4-thiazolyl)benzimidazole, p-chloromethaxylenol, benzyl bromoacetate, 2,3,5,6-tetrachloro-4-methylsulfonyl pyridine, N-dimethyl-N'-phenyl-(N'-fluorodichloromethlthio) sulfamide,2,4,5,6-tetrachloroisophthalonitrile,2,6-dichlorobenzonitrile,2-methyl-4-isothiazoline-3-one, manganese ethylenebisdithiocarbamate, zinc dimethyldithiocarbamate, 2-pyridinethiol-1-oxide (Zn salt), tetramethyl thiuram disulfide, 2,4,6-trichlorophenylmaleimide, 3-iodo-2-propalgylbutyl carbamate, diiodomethyl paratolyl sulfone, bisdimethyl dithiocarbamoyl zinc ethylene bisdithiocarbamate, phenyl (bispyridine) bismuth dichloride, 4-chlorophenyl-3-iodopropalgyl formal, 1,2-dibromo-2,4-dicyano-butane, N-(trichloromethylthio-4-cyclohexane-1,2-dicarboxyimide, 1-(methoxycarbonylamino) benzimidazole, dodecylbenzene sulfonic acid, parachloromethacresol, 2-(4-thiocyanomethylthio) benzothiazole, 2-methylthio-4,6-bis (ethylamino)-s-triazine, 2,4-dichlorophenoxy acetic acid, 2-methylthio-4-to-butylamino-6-cyclopropylamino-s-triazine, its salts or esters, and one or two such compounds may be included.

Incidentally, these antifouling/antifungal/antialgal agents are compounds which have been described in the aforementioned "Handbook of Agricultural Handbook, 1994 Edition" and "Dictionary of Antibacterial/antifungal agents" (edited by the Publishing Comittee of the Dictionary of Antibacterial/antifugal Agents, Aug. 22, 1986, published by Japanese Antibacterial and Antifungal Society).

Furthermore, the underwater antifouling composition of the second invention may be added in a paint to prepare an underwater antifouling paint, and this paint is coated, as before, on the surface of the underwater marine structure. And, if the constitutive materials of the underwater marine structure is a board or block made of synthetic resin or fibers, fishing net, cloth or net made of synthetic resin, the compounds may be added and mixed in the starting materials before molding or in the interior of the synthetic resin material by blending method, melt blending method or by impregnation method.

In case of adding the underwater antifouling composition directly in the synthetic resin material, total amount of the Compound A (or A') and Compound B (or C) to be added as the effective components in that composition is 0.1–10 weight %. Since the optimal amount to be added changes with the situation under which the underwater marine structure is to be defouled, it should be decided by individual preliminary tests. And, such method of preparation by which a solution or dispersion of the effective components of this composition is prepared in organic solvent, and then the fibers, net or cloth is dipped in this solution or dispersion to allow the/fiber substrate to absorb enough amount of the effective components of the composition, and then the organic solvent is removed from the fiber substrate by evaporation, can be used also as a way to add the underwater antifouling composition of the second invention in the natural or synthetic fibers, fishing net, woven or nonwoven clothes made from such fibers.

Examples of the underwater antifouling paint composition added with the underwater antifouling composition of the second invention are explained in the following Examples 5–10.

Examples 5–10 (Underwater antifouling paint)

A mixture of the Compound A 2 parts and the Compound B 2 parts was prepared, and then rosin 5 parts, acrylic resin 20 parts, xylene 40 parts, methylisobutyl ketone 20 parts, and calcium dodecylbenzne sulfonate 11 parts were added, and a total of 100 parts of this mixture were blended and dispersed in a ball mill for 5 hours, to obtain a homogeneous paint composition.

Using the same procedure as Example 5, components indicated in the following Table 1 were mixed at the indicated ratio, to prepare paint compositions of Examples 6–8, and the paint compositions of Comparative Examples 1–3 and Reference Example 1. These paint compositions were subjected to evaluation test of antifouling effect which will be described in the later examples of tests.

Incidentally, the paint composition in the Reference Example 1 is the example of the paint that does not contain the Compounds A, A', B and C which are effective components required in this invention. The paint compositions in Comparative Examples 1–3 contain either one of the compounds A, A', B or C.

TABLE 1

| Components in the paint composition | | | | | | | | | | | |
|---|---|---|---|---|---|---|---|---|---|---|---|
| Type of components in the paint | Name of the component | Composition of paint (weight parts) | | | | | | | | | |
| | | Examples | | | | | | Comparative Examples | | | Reference |
| | | 5 | 6 | 7 | 8 | 9 | 10 | 1 | 2 | 3 | Example 1 |
| Basic components for paint | Acrylic resin | 20 | 20 | 20 | 20 | 20 | 20 | 20 | 20 | 20 | 20 |
| | Rosin | 5 | 5 | 5 | 5 | 5 | 5 | 5 | 5 | 5 | 5 |
| | Xylene | 40 | 40 | 40 | 40 | 40 | 40 | 40 | 40 | 40 | 40 |
| | Methylisobutyl ketone | 20 | 20 | 20 | 20 | 20 | 20 | 20 | 20 | 20 | 20 |
| Effective components for antifouling action | Compound A | 2 | 1 | 2 | 1 | 0 | 0 | 2 | 0 | 0 | 0 |
| | Compound A' | 0 | 0 | 0 | 0 | 2 | 2 | 0 | 0 | 0 | 0 |
| | Compound B | 2 | 1 | 0 | 0 | 2 | 0 | 0 | 2 | 0 | 0 |
| | Compound C | 0 | 0 | 2 | 1 | 0 | 2 | 0 | 0 | 2 | 0 |
| Surface activating agent | Calcium dodecylbenzene sulfonate | 11 | 13 | 11 | 13 | 11 | 11 | 13 | 13 | 13 | 15 |

Examples of the test for the preservative antifungal effect of the industrial preservative/antifungal composition of the first invention and the underwater antifouling effect of the underwater antifouling composition of the second invention are illustrated in the following.

Example of Test 1 (Antibacterial test)

Compound A, Compound A', Compound B and Compound C, alone or in a combination of two, were used and dissolved in acetone to create several kinds of solution having different concentrations. Media containing one or two kinds of test compounds in a certain concentration was prepared by mixing 1 ml of the solution with 10 ml of the medium (Potato agar, pH 5.8, was used for testing fungi and yeasts, and meat broth agar, pH 7.0, was used for testing bacteria). One loopful of spore suspensin of the culture of test microorganisms which were pre-cultured in agar slant (cultivated at 28° C. for 7 days for fungi and yeast, and 30° C. for 2 days for the bacteria) was inoculated on the media containing the test compound, by streaking with a platinum loop. After inoculation, fungi and yeasts were cultivated at 24° C. for 72 hours, and bacteria were cultivated at 30° C. for 48 hours. Growth of test microorganisms in the media was examined. Minimum growth inhibitory concentration (ppm) of the test compound, required to completely inhibit the growth of test microorganism in the media, was calculated.

Using a media that contained either one of the Compound A or Compound B or both as the test compound, following microorganisms were cultured: *Penicillium funiculosum, Aureobasidium pullulans, Bacillus subtilis. Pseudomonas aeruginosa, Staphylococcus aureus, Saccharomyces cerevisiae*.

Fungus, bacteria, or yeast was cultivated in the media that contained the Compound A alone as the effective bactericidal component, media that contained the Compound B alone as the supplementary agent, or the media that contained Compound A and Compound B in a weight ratio of 3:1, 1:1, or 1:3, under the above-said condition, and minimum inhibitory concentration (MIC, ppm) of the fungi, bacteria or yeast was determined. Results are presented in Table 2.

TABLE 2

| | Minimum inhibitory concentration (MIC, ppm) | | | | |
|---|---|---|---|---|---|
| | | | MIC, using a mixture of Compound A and Compound B Mixing ratio | | |
| Test | Compound | Compound | | | |
| microorganism | A | B | 3:1 | 1:1 | 1:3 |
| Penicillum funiculosum | 0.5 | 300 | 0.5 | 0.5 | 0.5 |
| Aureobasidium pullulans | 1.0 | 300 | 0.5 | 1.0 | 1.0 |
| Bacillus subtilis | 0.5 | 300 | 0.5 | 0.5 | 0.25 |
| Staphylococcus aureus | 1.0 | 300 | 1.0 | 1.0 | 0.25 |
| Pseudomonas aeruginosa | 2.0 | 300 | 2.0 | 2.0 | 1.0 |
| Saccharomyces cerevisiae | 0.25 | 300 | 0.25 | 0.25 | 0.25 |

In the above-described cultivation test, bactericidal effect of the Compound A increased significantly or synergistically when it was used together with the Compound B which had a very weak bactericidal activity and when the weight ratio of the Compound A and the Compound B was in 3:1, 1:1, or 1:3 range.

When the cultivation test of bacterria was repeated by using the Compound A' instead of the Compound A, the bactericidal effect of the Compound A' was found to increase by adding the Compound B, in the same trend as before.

Furthermore, the media containing the Compound A alone as the effective bactericidal component, the media containing the Compound C alone as the supplementary agent component, or the media containing both Compound A and Compound C in a weight ratio of 3:1, 1:1, or 1:3 were used, respectively, to cultivate fungi, bacteria or yeasts under the same condition. Minimum inhibitory concentration (MIC, ppm) of the cultured fungi, bacteria or yeasts is shown in Table 3. *Aspergillus niger, Penicillium citrinum, Cladosporium cladosporioides, Enterobacter aerogenes, Klebsiella pneumoniae*, and *Rhodotorula mucilaginosa* were used in this cultivation test.

TABLE 3

| | Minimum inhibitory concentration (MIC, ppm) | | | | |
|---|---|---|---|---|---|
| | | | MIC, using a mixture of Compound A and Compound C Mixing ratio | | |
| Test | Compound | Compound | | | |
| microorganism | A | B | 3:1 | 1:1 | 1:3 |
| Aspergillus niger | 0.5 | 300 | 0.5 | 0.5 | 0.5 |
| Penicillium citrinum | 1.0 | 300 | 0.5 | 0.5 | 1.0 |
| Cladosporium cladosporioides | 1.0 | 200 | 0.5 | 0.5 | 1.0 |
| Enterobacter aerogenes | 0.5 | 100 | 0.5 | 0.5 | 0.5 |
| Klebsiella pneumoniae | 2.0 | 300 | 2.0 | 1.0 | 1.0 |
| Rhodotorula mucilaginosa | 1.0 | 300 | 1.0 | 2.0 | 4.0 |

In this cultivation test, the bactericidal effect of the Compound A was found to increase significantly or synergistically when the Compound C that has only a very weak bactericidal activity was added also and when the weight ratio of the Compound A and the Compound C was in 3:1, 1:1, or 1:3 range.

Example of Test 2 (Test for antibacterial/antifungal effect of vinyl acetate resin emulsion paint)

An emulsion containing both Compound A and Compound B, emulsion containing Compound A and Compound C, and emulsion containing either one of the Compound A, B, or C were prepared by the procedure of Example 1.

These emulsions were added to the white paint in such a way that the concentration of active ingredient will remain at a constant level, and they were agitated and mixed in a homogenizer for 30 seconds, to prepare the antifouling paint.

A spiled sample of emulsion paint was used as the seed bacteria, and it was insulated (1%) into the thus-prepared paint. The inoculated paint was sealed in a can and stored at 35° C. for 1 month.

After one months of storage, additional amount (1%) of the spiled sample of emulsion paint was added every day, and it was cultured secondarily at 35° C. for 4 days. During this 4 day period, sample was removed daily from the secondarily cultivated paint fluid, and number of microorganisms survived in the sample was determined. Results are presented in Table 4.

TABLE 4

| Examples of test | Compound added in the emulsion | Amount of emulsion added (weight %) | Concentration of the compound in the paint sample (ppm) | | | Number of cells survived in the spoiled paint (viable cells/ml) | | | |
|---|---|---|---|---|---|---|---|---|---|
| | | | | | | Length of secondary cultivation (days) | | | |
| | | | Compound A | Compound B | Compound C | 1 | 2 | 3 | 4 |
| Example of Test 2-1 (This invention) | Compound A + Compound B | 0.2 0.1 | 200 100 | 200 100 | 0 0 | 0 0 | 0 0 | 0 0 | 0 0 |
| Example of Test 2-2 (This invention) | Compound A + Compound C | 0.2 0.1 | 200 100 | 0 0 | 200 100 | 0 0 | 0 0 | 0 0 | 0 0 |
| Comparative Example of Test 1 | Compound A | 0.2 0.1 | 200 100 | 0 0 | 0 0 | 0 $3 \times 10^2$ | 0 $>10^6$ | $2 \times 10^4$ $>10^6$ | $>10^6$ " |
| Comparative Example of Test 2 | Compound B | 0.2 0.1 | 0 0 | 200 100 | 0 0 | $>10^6$ $>10^5$ | $>10^6$ " | $>10^6$ " | $>10^6$ " |
| Comparative Example of Test 3 | Compound C | 0.2 0.1 | 0 0 | 0 0 | 200 100 | $>10^6$ " | $>10^6$ " | $>10^6$ " | $>10^6$ " |
| Reference Example of Test 1 | No addition | 0 | 0 | 0 | 0 | $>10^6$ | $>10^6$ | $>10^6$ | $>10^6$ |

As clearly demonstrated in the result shown in Table 4, the number of putrefying microorganisms survived in the paint sample by the end of the test period was zero with the paint sample prepared by combining the Compound A and Compound B (or Compound C) according to the first invention, and thus paint was preserved perfectly. In contrast, with the paint sample for comparison which contained only Compound A, B or C alone at the same concentration and the paint sample without such compound, the number of surviving microorganisms at the end of the test period was more than $10^6$/ml, and thus the paint was spoiled.

Example of Test 3 (Field breakdown test with vinyl acetate resin emulsion paint)

The flowable agents containing the Compound A and Compound B or Compound C, or containing only one of these compounds were prepared by the procedure of Example 4. These Flowable agents were added to the white paint of vinyl acetate resin emulsion in an amount indicated in Table 5, and then it was mixed thoroughly, to prepare the paint.

The paint was kept in a 1 kg capacity can and stored at room temperature. Condition of the paints after 3 month, after 6 months, and after 12 months was examined. Results are presented in Table 5.

TABLE 5

| Example of test | Compound used in the flowable agent | Amount of flowable agent added (weight %) | Concentration of the test compound in paint sample (ppm) | | | Condition of paint | | |
|---|---|---|---|---|---|---|---|---|
| | | | | | | Storage period (months) | | |
| (This invention) | | | Compound A | Compound B | Compound C | 3 | 6 | 12 |
| Example of Test 3-1 (This invention) | Compound A + Compound B | 0.2 0.1 | 200 100 | 400 200 | 0 0 | Normal " | Normal " | Normal " |
| Example of Test 3-2 (This invention) | Compound A + Compound C | 0.2 0.1 | 200 100 | 0 0 | 400 200 | Normal " | Normal " | Normal " |
| Comparative Example of Test 4 | Compound A | 0.4 0.2 | 400 200 | 0 0 | 0 0 | Normal Poor | Normal Poor | Normal Poor |
| Comparative Example of Test 5 | Compound B | 0.4 0.2 | 0 0 | 800 400 | 0 0 | Poor " | Poor " | Poor " |
| Comparative Example of Test 6 | Compound C | 0.4 0.2 | 0 0 | 0 0 | 800 400 | Poor " | Poor " | Poor " |
| Reference Example of Test 2 | No addition | 0 | 0 | 0 | 0 | Poor | Poor | Poor |

Example of Test 4 (Test for antimicrobial effect with starch paste)

An emulsion prepared by adding either one of the Compound A or Compound B (or Compound C) was mixed with tapioca starch 15 parts by the procedure of the Example 1, to prepare an aqueous solution 85 parts that contained the compound in an amount indicated in Table 6. The mixture was placed in a 200 ml flask. While the mixture was agitated, it was heated to 70° C., and then was allowed to cool down slowly, to prepare a starch paste. Then, a spoiled starch paste (1%) was added to inoculate the microorganisms, and then the inoculated material was stored at 37° C.

During the 4 weeks of storage period, number of surviving microorganisms was determined every other week. Results are presented in Table 6.

Compound C was added alone at the concentration shown in Table 6, was spoiled completely by the end of the test period, except the sample to which 200 ppm of the Compound A was added.

Example of Test 5 (Spoilage test with casein)

Emulsions prepared by adding such an amount of Compound A or Compound B (or Compound C) or both, shown in Table 7, to casein in 10 parts, were prepared by the procedure of Example 2, and then ammonia water 2 parts were added, and then the total volume was brought up to 100 parts with water. The thus-obtained mixture was placed in a 200 ml flask. While the mixture was agitated in the flask, it was heated to 80° C., and then allowed to cool slowly, to prepare a casein solution. This solution was placed in a beaker and covered with an aluminum foil, and stored in a

TABLE 6

| Examples of test | Compound added in the emulsion | Amount of emulsion added (weight %) | Concentration of the compound in the starch sample (ppm) | | | Number of cells survived in the starch sample (viable cells/ml) | | | |
|---|---|---|---|---|---|---|---|---|---|
| | | | Compound A | Compound B | Compound C | Cultivation period (weeks) | | | |
| | | | | | | 1 | 2 | 3 | 4 |
| Example of Test 4-1 (This invention) | Compound A + Compound B | 0.1 0.05 | 100 50 | 100 50 | 0 0 | 0 0 | 0 0 | 0 0 | 0 0 |
| Example of Test 4-2 (This invention) | Compound A + Compound C | 0.1 0.05 | 100 50 | 0 0 | 100 50 | 0 0 | 0 0 | 0 0 | 0 0 |
| Comparative Example of Test 7 | Compound A | 0.1 0.05 | 100 50 | 0 0 | 0 0 | 0 $10^2$ | 0 $10^6$ | $2 \times 10^4$ $>10^6$ | $>10^6$ $>10^6$ |
| Comparative Example of Test 8 | Compound B | 0.1 0.05 | 0 0 | 100 100 | 0 0 | $>10^6$ " | $>10^6$ " | $>10^6$ " | $>10^6$ " |
| Comparative Example of Test 9 | Compound C | 0.1 0.05 | 0 0 | 0 0 | 100 50 | $>10^6$ " | $>10^6$ " | $>10^6$ " | $>10^6$ " |
| Reference Example of Test 1 | No addition | 0 | 0 | 0 | | $>10^6$ | $>10^6$ | $>10^6$ | $>10^6$ |

As clearly demonstrated by the results shown in Table 6, the starch paste sample to which a combination of the Compound A and Compound B (or Compound C) of this invention was added in the concentrations shown in Table 6, was not spoiled after the lengthy test period. In contrast, the starch paste sample to which Compound A, Compound B or Compound C was added alone at the concentration shown in Table 6, was spoiled completely by the end of the test period, except the sample to which 200 ppm of the Compound A was added.

30° C. incubator. After culturing the naturally born microorganisms, sample (1 ml) was taken from the casein solution on the 10th day and 20th day, and number of surviving microorganisms was determined. Results are presented in Table 7.

TABLE 7

| Examples of test | Compound added in the emulsion | Amount of emulsion added (weight %) | Concentration of test compound in gelatin solution (ppm) | | | Number of cells survived in gelatin solution (viable cells/ml) | |
|---|---|---|---|---|---|---|---|
| | | | Compound A | Compound B | Compound C | Cultivation period (days) | |
| | | | | | | 10 | 20 |
| Example of Test 5-1 (This invention) | Compound A + Compound B | 0.04 0.02 0.01 | 80 40 20 | 40 20 10 | 0 0 0 | 0 0 0 | 0 0 0 |
| Example of Test 5-2 (This invention) | Compound A + Compound C | 0.04 0.02 0.01 | 80 40 20 | 0 0 0 | 40 20 10 | 0 0 0 | 0 0 0 |
| Comparative | Compound A | 0.04 | 80 | 0 | 0 | $3.4 \times 10^6$ | $>10^6$ |

TABLE 7-continued

| Examples of test | Compound added in the emulsion | Amount of emulsion added (weight %) | Concentration of test compound in gelatin solution (ppm) | | | Number of cells survived in gelatin solution (viable cells/ml) | |
|---|---|---|---|---|---|---|---|
| | | | Compound A | Compound B | Compound C | Cultivation period (days) | |
| | | | | | | 10 | 20 |
| Example of Test 10 | | 0.02 | 40 | 0 | 0 | >10$^6$ | " |
| Comparative Example of Test 11 | Compound B | 0.04 | 0 | 40 | 0 | >10$^6$ | >10$^6$ |
| | | 0.02 | 0 | 20 | 0 | " | " |
| Comparative Example of Test 12 | Compound C | 0.04 | 0 | 0 | 40 | >10$^6$ | >10$^6$ |
| | | 0.02 | 0 | 0 | 20 | " | " |
| Reference Example of Test 4 | No addition | 0 | | 0· | | >10$^6$ | >10$^6$ |

As clearly demonstrated by the results shown in Table 7, the aqueous gelatin solution to which the Compound A and Compound B (or Compound C) were added together at the concentration shown in Table 7, did not spoil after storing in air at 30° C. for 20 days. However, when Compound B or Compound C was added alone, the aqueous casein solution was spoiled by the end of the test period.

Example of Test 6 (Antifouling test with fishing net)

The fishing net used in the present test was a square fishing net (20 cm ×20 cm) made from polyethylene filaments. Each edge of the net had 9 knots. Several such fishing nets were prepared. An iron rod (diameter=5 mm) was bended to fabricate a square frame (one edge was 60 cm), and the area surrounded by the frame was divided into four equal sections. A test net was stretched in each section.

Paints containing one or both Compound A and Compound B (or Compound C) at the concentration (weight %) shown in Table 8 were prepared by the procedure of Example 5. Each paint was coated on the surface of the polyethylene filaments of the net (amount coated=an average of 6 g per net).

Separately, after melting and blending the test compound (s) in the polyethylene resin which was the raw material used for preparation of the polyethylene filaments of the net, the polyethylene resin was spinned and the filaments were used to make a net. This net, without coating the paint, was used also for the test.

The iron frames stretched with these test fishing nets were suspended horizontally in a depth of 1 m under the water by means of a polyethylene rope.

The test net was set in the red snapper culturing fram in the ocean near the Northern Kyushu. Test fishing net was set in a divided crawl, to run the test for 6 months from May 1, 1994.

To evaluate the antifouling effect, the number of months until the attached marine organisms covered the whole surface area of the fishing net was taken as the effective antifouling period. The bioecology of the fishing net coated with the paint containing no test compound was compared with that of the fishing net fabricated by using he polyethylene filaments containing the compound(s).

During this test period, bacteria and diatoms started to adhere within 2 weeks from the starting date of test. Later, *Mytilus edulis*, *Balnus sp.* and *Ulva sublittoralis* attached on the net at almost the same time. Largest number of marine organisms attached on the net during the 7 month–8 month period, and *Bugula neritina* was the dominant species. And, *Hydroides norvegicus* attached densely in the underlayer.

Later, *Bugula neritina* detached from the net, and the number of *Mytilus edulis* increased as they grew. At the end of the test period, large organisms such as *Styela plicata*, *Hvdroides norvegicus*, and *Mytilus edulis* dominated the population.

Results are presented in Table 8.

TABLE 8

| Examples of test | Compound tested | Concentration of the compound added to paint or the polyethylene resin used for making filaments (%) | | | Effective period of antifouling agent (months) | |
|---|---|---|---|---|---|---|
| | | Compound A | Compound B | Compound C | Test with fishing net coated with the paint | Test with fishing net made from polyethylene filaments containing a blend of test compound |
| Example of Test 6-1 | Compound A + Compound B | 2 | 2 | 0 | More than 6 | More than 6 |
| Example of Test 6-2 | Compound A + Compound B | 1 | 1 | 0 | More than 6 | More than 6 |
| Example of Test 6-3 | Compound A + Compound C | 2 | 0 | 2 | More than 6 | More than 6 |
| Example of Test 6-4 | Compound A + Compound C | 1 | 0 | 1 | More than 6 | More than 6 |

TABLE 8-continued

| Examples of test | Compound tested | Concentration of the compound added to paint or the polyethylene resin used for making filaments (%) | | | Effective period of antifouling agent (months) | |
|---|---|---|---|---|---|---|
| | | Compound A | Compound B | Compound C | Test with fishing net coated with the paint | Test with fishing net made from polyethylene filaments containing a blend of test compound |
| Comparative Example of Test 13 | Compund A | 2 | 0 | 0 | More than 6 | More than 6 |
| Comparative Example of Test 14 | Compound A | 1 | 0 | 0 | 3 | 3 |
| Comparative Example of Test 15 | Compound B | 0 | 2 | 0 | 1 | 1 |
| Comparative Example of Test 16 | Compound B | 0 | 1 | 0 | 1 | 1 |
| Comparative Example of Test 17 | Compound C | 0 | 0 | 2 | 1 | 1 |
| Comparative Example of Test 18 | Compound C | 0 | 0 | 1 | 1 | 1 |
| Reference Example of Test 5 | | No addition | | | 1 | 1 |

As clearly shown in Table 8, the result with Compound B or Compound C alone was basically the same as the result obtained for the control in the Example of Test 5, and antifouling effect seemed to be absent. In contrast, when Compound A and Compound B were combined at 1:1 weight ratio and added in the paint or in the polyethylene resin, the antifouling effect with 1% of Compound A alone was basically identical to the antifouling effect with 2% of Compound A alone. Thus, addition of a combination of Compound B or Compound C and Compound A has an effect to reduce the amount of Compound A required to achieve enough antifouling effect. And, since coating the paint containing the test compound on the fishing net or blending the test compound in the filaments used to form the fishing net did not show a difference in its antifouling effect, it is confirmed that the antifouling action of the Compound A is increased synergistically by combining Compound A with the Compound B or Compound C for both cases.

Following effects were created by using the industrial preservative antifungal composition of the first invention.

First, the composition of the first invention prevents growth of various microorganisms such as bacteria, yeasts and fungi, nonselectively and thoroughly. Therefore, it can be used widely as the industrial preservative antifungal agent. Secondly, it shows a potent preservative antifungal effect, even with a very small amount of agent. Thirdly, it provides, even with a small amount, a high preservative antifungal effect for a long period of time. Fourthly, it has a low toxicity to human and animals. And, Fifthly, it can be used in industrial resource materials such as industrial raw materials or products by employing various methods such as by spraying, coating, mixing, and so on. With any of these methods, it will never cause a harm to the industrial resource material.

Since the industrial preservative antifungal composition of this invention has the above-described properties, it can be used widely as a preservative antifungal agent for various industrial raw materials or products for many purposes whose examples are illustrated in the following.

(1) Prevention of spoilage caused by growth of bacteria, fungi, and yeasts during production, storage and use of water-based or oil-based paint, and prevention of fouling of the coated surface caused by growth of filamentous fungi.

(2) Prevention of spoilage of adhesives or pastes such as casein, polyvinyl alcohol, starch, etc. caused by growth of bacteria, fungi and yeasts, and prevention of fouling of the coated or adhesion surface caused by filamentous fungi.

(3) Prevention of deterioration of quality of raw materials to be used for production of paper such as wet pulp and chips during its storage caused by growth of bacteria, fungi and yeasts.

(4) Prevention of fouling and deterioration of quality of processed products such as woods, plywoods, bamboo materials and leathers, and other materials, caused by growth of filamentous fungi.

(5) Prevention of fouling and deterioration of quality of natural fibers, synthetic fibers, its mixed spin products and related materials, caused by growth of bacteria, fungi and yeasts.

(6) Prevention of deterioration of quality of synthetic emulsion or emulsion tacks, caused by growth of bacteria, fungi and yeasts.

(7) Prevention of deterioration of quality of concrete mix, caused by growth of bacteria, fungi and yeasts.

(8) Prevention of deterioration of the quality of cutting oil, etc., caused by growth of bacteria, fungi, and yeasts.

(9) Prevention of deterioration of the quality of plastic, rubber, etc., caused by growth of bacteria, fungi, and yeasts.

(10) An agent to control the slime caused mainly by bacteria, fungi and algae, during the paper making process.

And, following effects can be created by using the underwater antifouling composition of the second invention.

Attachment of marine organisms such as Balnus, Ascidia Hydrozoa, Mytilus, Cristaria, Bugula, Hydroids, Ulva, and Enteromorpha can be prevented for a long period of time by coating the paint containing the underwater antifouling composition of the second invention on the underwater marine structure or by mixing and adding the underwater antifouling composition in the constitutive material to be used in the underwater marine structure. And, the antifouling effect and the sustaining periods of the composition was far greater or longer than when the Compound A, B, or C of this invention was used alone. The component of Compound A, B or C to be used in this invention has a very low toxicity to human, animals and fishes, and therefore they can be used safely.

What is claimed is:

1. Preservative composition comprising a synergistic mixture of antifungal industrial preservatives consisting essentially of:

(A) one or more compounds selected from: 4,5-dichloro-2-n-octyl-4-isothiazolin-3-one, 2-n-octyl-4-isothiazolin-3-one, and salts thereof, and (B) one or more compounds selected from: 5-[2-(2-butoxyethoxy) ethoxymethyl]-6-propyl-1,3-benzodioxole and octachlorodipropyl ether, wherein the concentration of the mixture of antifungal industrial preservatives is at least 0.1 weight %, and the weight ratio of (A):(B) is from 1:0.1 to 1:5.

2. The composition of claim 1 wherein the weight ratio of (A):(B) is from 1:0.3 to 1:3.

3. The composition of claim 1 further comprising a carrier selected from: mineral powders, plant powders, alumina, silicate salts, sugar polymers, highly dispersed silicic acid, waxes, semi-solid oils, water, alcohols, aromatic hydrocarbons, halogenated hydrocarbons, ethers, ketones, esters, nitrites, sulfoxides, glycol ethers, amines, aliphatic or alicyclic hydrocarbons, industrial gasoline, and petroleum fractions.

4. The composition of claim 1 further comprising a supplementary agent selected from: surface active agents, binders and stabilizers.

5. Underwater antifouling composition comprising:

a synergistic mixture of antifouling compounds consisting essentially of: (A) one or more compounds selected from: 4,5-dichloro-2-n-octyl-4-isothiazolin-3-one, 2-n-octyl-4-isothiazolin-3-one, and salts thereof, and (B) one or more compounds selected from: 5-[2-(2-butoxyethoxy) ethoxymethyl]-6-propyl-1,3-benzodioxole and octachlorodipropyl ether; and a film forming agent;

wherein the concentration of the mixture of antifouling compounds is at least 0.1 weight %, and the weight ratio of (A):(B) is from 1:0.1 to 1:10.

6. The composition of claim 3 wherein the weight ratio of (A):(B) is from 1:1 to 1:3.

7. The composition of claim 5 wherein the film forming agent is selected from: vinylchloride/vinyl acetate copolymers, vinylchloride/vinylisobutyl ether copolymers, styrene/butadiene copolymers, chlorinated rubber resins, chlorinated polypropylene resins, petroleum resins, alkyd resins, acrylic resins, phenolic resins, synthetic rubber, epoxy resins, silicone rubber, silicon resins, and rosin resins.

* * * * *